US006545488B2

United States Patent
Yamagishi et al.

(10) Patent No.: US 6,545,488 B2
(45) Date of Patent: Apr. 8, 2003

(54) PIPING FLUID DECISION DEVICE AND PIPING FLUID CONTROL SYSTEM

(75) Inventors: Junichi Yamagishi, Tokyo (JP); Eikou Yo, Tokyo (JP)

(73) Assignee: Unirec Co., Ltd., Tokyo (JP)

( * ) Notice: Subject to any disclaimer, the term of this patent is extended or adjusted under 35 U.S.C. 154(b) by 0 days.

(21) Appl. No.: 09/870,355

(22) Filed: May 30, 2001

(65) Prior Publication Data

US 2002/0118025 A1 Aug. 29, 2002

(30) Foreign Application Priority Data

Feb. 26, 2001 (JP) ........................................ 2001-050747

(51) Int. Cl.$^7$ .............................................. G01N 33/18
(52) U.S. Cl. ........................ 324/672; 73/61.41; 361/178
(58) Field of Search ................................ 324/458, 665, 324/667, 672; 73/61.41, 861.04, 861.08; 361/178

(56) References Cited

U.S. PATENT DOCUMENTS

| 3,770,020 A | * | 11/1973 | Tamura et al. ............ 137/487.5 |
| 3,826,979 A | * | 7/1974 | Steinmann ................ 200/61.05 |
| 4,487,057 A | * | 12/1984 | Lutz .......................... 174/11 R |
| 4,751,842 A | * | 6/1988 | Ekrann et al. ............... 324/662 |
| 4,752,727 A | * | 6/1988 | Schneider .................... 324/178 |
| 4,832,503 A | * | 5/1989 | Dowling et al. ............ 374/135 |
| 5,035,139 A | * | 7/1991 | Hoefelmayr et al. ......... 73/1.73 |
| 5,423,206 A | * | 6/1995 | Hetzel ....................... 73/304 C |
| 5,503,027 A | * | 4/1996 | Hemp ....................... 73/861.11 |
| 5,503,035 A | * | 4/1996 | Itoh et al. ................. 73/861.19 |
| 5,935,433 A | * | 8/1999 | Stefanini .................... 210/222 |
| 6,097,587 A | * | 8/2000 | Inagawa et al. ............. 361/502 |

FOREIGN PATENT DOCUMENTS

| JP | 10-332312 | 12/1998 |
| JP | 11-067033 | 3/1999 |

* cited by examiner

Primary Examiner—N. Le
Assistant Examiner—Vincent Q. Nguyen
(74) Attorney, Agent, or Firm—Kilpatrick Stockton LLP

(57) ABSTRACT

To enable a fluid state of a fluid substance flowing through a path in a piping, for example a liquid state or a froth state of beer, to be surely and easily judged while keeping a sanitary condition, allowing a take out to be surely and easily performed, a piping fluid decision device is constituted with an electrostatic capacity sensor (15) disposed outside of a piping (1) adapted for a fluid substance to flow through a path therein, for detecting a variation of electrostatic capacity of the path in the piping (1), reference value storage means for storing in advance a reference variation of electrostatic capacity of the path to provide for a decision on a fluid state of the fluid substance flowing through the path in the piping, and fluid decision means for comparing the detected variation of electrostatic capacity and the stored variation of electrostatic capacity to make the decision on the fluid state of the fluid substance flowing through the path.

3 Claims, 7 Drawing Sheets

RELEVANT ART

US 6,545,488 B2

PIPING FLUID DECISION DEVICE AND PIPING FLUID CONTROL SYSTEM

BACKGROUND OF THE INVENTION

1. Field of the Invention

The present invention relates to a piping fluid decision device adapted for a decision of a fluid state of a fluid substance such as a liquid flowing in a piping, and a piping fluid control system for controlling the fluid state of the fluid substance depending on result of the decision.

2. Description of Relevant Art

Conventionally, as an example of such a device, there is one decides a fluid state of beer in a piping for sending beer in a beer factory or food shop. For example, as shown in FIG. 1, electrodes 103 and 105 are inserted in a piping 101 for sending beer, and a decision is made on a fluid state of beer 107 flowing in the piping 101. The decision of the fluid state is made by detecting a conductivity in the piping 101 using the electrodes 103 and 105, and detecting a difference of conductivity between a liquid part 109 and a froth part 111 of the beer 107. Depending on a result of the decision, the froth part 111 of the beer 107 flowing in the piping 101 is wasted, as necessary, to surely take out the liquid part 109 of the beer.

Therefore, it is possible to take out beer 107 with little froth anytime from a take-out machine installed at a terminal of the piping 101.

However, in the conventional device of FIG. 1, beer 107 flowing in the piping 101 directly contacts the electrodes 103 and 105, thus easily leading to corrosion of the electrode 103 and 105, with a probable sanitary problem. As a variation of conductivity is detected, voltage variations to be small are necessarily integrated, with an increased calculation amount, as another problem. The detection by conductivity tends to be influenced by an associated magnetic field, and eliminates a disposition in a vicinity of an electromagnetic valve, as still another problem.

Further, if the fluid substance flowing in the piping .101 is a solid body such as a metallic flow, a soil flow, or a stone flow, the fluid substance may collide on the electrodes 103 and 105, causing the electrodes 103 and 105 to be damaged, leading to a probable failure of detection. Therefore, it was difficult, for a device having electrodes 103 and 105 inserted in a piping 101 like FIG. 1, to make a decision on a fluid state of a solid fluid substance.

SUMMARY OF THE INVENTION

The present invention has been made with such points in view. It therefore is an object of the present invention to provide a piping fluid decision device and a piping fluid control system that can surely and easily make a decision on a fluid state of a fluid substance flowing in a piping, irrespective of the kind, without sanitary problem.

To achieve the object, according to a first aspect of the invention, there is provided a piping fluid decision device comprising an electrostatic capacity sensor disposed outside of a piping adapted for a fluid substance to flow through a path therein, for detecting a variation of electrostatic capacity of the path in the piping, reference value storage means for storing in advance a reference variation of electrostatic capacity of the path to provide for a decision on a fluid state of the fluid substance flowing through the path in the piping, and fluid decision means for comparing the detected variation of electrostatic capacity and the stored variation of electrostatic capacity to make the decision on the fluid state of the fluid-substance flowing through the path.

According to a second aspect of the invention, in a piping fluid decision device according to the first aspect of the invention, the electrostatic capacity sensor comprises a measuring electrode and a grounding electrode made of a conductive metallic film and wound around an outside of the piping forming the path, with an insulator in between, and a shield member covering the measuring electrode and the grounding electrode, with an insulator in between.

According to a third aspect of the invention, in a piping fluid decision device according to the second aspect of the invention, the grounding electrode is narrower than the measuring electrode, and the measuring electrode and the grounding electrode are alternately disposed.

According to a fourth aspect of the invention, in a piping fluid decision device according to the third aspect of the invention, the measuring electrode and the grounding electrode are wound to be spiral along a flow direction.

Further to achieve the object, according to a fifth aspect of the invention, there is provided a piping fluid control system comprising a piping fluid decision device according to any of the first to fourth aspects of the invention, adjust means adapted to adjust the fluid state of the fluid substance flowing through the path, and control means for controlling the adjust means depending on a result of the decision of the fluid decision means.

According to a sixth aspect of the invention, in a piping fluid control system according to the fifth aspect of the invention, the piping is provided at a terminal thereof with a substance take-out machine of the fluid substance, the adjust means comprises a first open-close valve installed on the piping between an electrostatic capacity sensor position and a substance take-out machine position, and a second open-close valve installed on a branch pipe connected to the piping between a position of the first open-close valve and the electrostatic capacity sensor position, and the control means is adapted, when the variation of electrostatic capacity is within a set value, to open the first open-close valve and close the second open-close valve and, when the variation of electrostatic capacity exceeds the set value, to close the first open-close valve and open the second open-close valve.

According to the first aspect of the invention, for a fluid substance flowing through a path in a piping, a variation of electrostatic capacity of the path in the piping can be detected by an electrostatic capacity sensor. Reference value storage means can store in advance a reference variation of electrostatic capacity of the path to provide for a decision on a fluid state of the fluid substance flowing through the path in the piping. Fluid decision means can compare the detected variation of electrostatic capacity and the stored variation of electrostatic capacity to make the decision on the fluid state of the fluid substance flowing through the path.

Accordingly, a decision can surely be made of a fluid state in a piping, for example, such as on a normality or abnormality or of a change of kind of fluid substance. Moreover, fluid state of a fluid substance flowing through a path in a piping can be intact-decided, securing a sanitary condition even when the fluid substance is a food. Further, fluid state of a fluid substance flowing in a path can be decided by an electrostatic capacity or its variation, with a large voltage variation without needing an integration of detected values, and with a reduced calculation amount. As the fluid state is detected by a variation of electrostatic capacity, it hardly receive influences of a magnetic field. Even when the fluid substance is a slid body, such as a metallic flow, soil flow, stone flow, or the like, electrodes are kept from collision with the fluid substance, allowing for a fluid state of solid fluid substance to be surely and easily decided.

According to the second aspect of the invention, in addition to effects of the first aspect of the invention, a fluid state of a fluid substance in a piping can be surely and easily decided by a measuring electrode and a grounding electrode of a conductive metallic film wound in turns, securing a sanitary condition as well.

According to the third aspect of the invention, in addition to effects of the second aspect of the invention, because the grounding electrode is narrower than the measuring electrode and the measuring electrode and the grounding electrode are alternately disposed, the fluid state of a fluid substance flowing in the piping can be decided in a more ensured manner.

According to the fourth aspect of the invention, in addition to effects of the third aspect of the invention, because the measuring electrode and the grounding electrode are wound to be spiral along a flow direction, the fluid state of a fluid substance flowing in the piping can be decided in a more ensured and facilitated manner.

According to the fifth aspect of the invention, in addition to effects of the first to fourth aspects of the invention, depending on a result of the decision of the fluid state, control means is adapted to control adjust means, so that the fluid state of a fluid substance flowing in the path can be surely and easily controlled.

According to the sixth aspect of the invention, in addition to effects of the fifth aspect of the invention, the control means is adapted, when the detected variation of electrostatic capacity is within a set value of a reference variation of electrostatic capacity, to open the first open-close valve and close the second open-close valve and, when the detected variation of electrostatic capacity exceeds the set value of the reference variation of electrostatic capacity, to close the first open-close valve and open the second open-close valve.

Accordingly, when the fluid state of a fluid substance flowing through the path in the piping is normal or the fluid substance is not changed in kind and if the detected variation of electrostatic capacity is within a set value of a reference variation of electrostatic capacity, it is possible to conduct the fluid substance from the piping to a substance take-out machine and surely take out of the substance take-out machine the fluid substance of a normal fluid state or of an unchanged kind. Further, when the fluid state of a fluid substance flowing through the path in the piping is abnormal or the fluid substance is changed in kind and if the detected variation of electrostatic capacity exceeds the set value of the reference variation of electrostatic capacity, it is possible to- stop conducting the fluid substance from the piping to the substance take-out machine and surely conduct the fluid substance of an abnormal fluid state or of a changed kind to a branch pipe end.

BRIEF DESCRIPTION OF THE ACCOMPANYING DRAWINGS

DETAILED DESCRIPTION OF THE PREFERRED EMBODIMENTS

Figure 1:
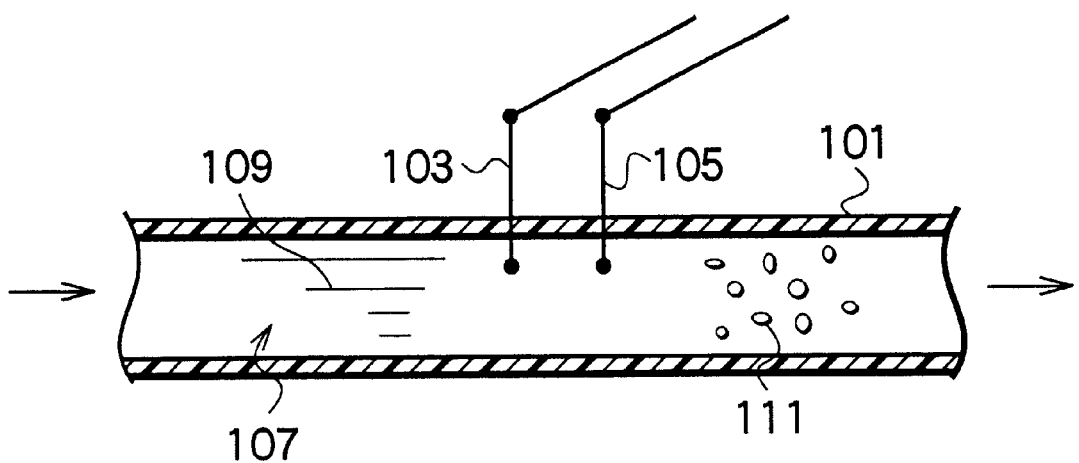
FIG. 1 is a schematic fragmentary illustration for explanation of a conventional piping fluid controller.
Figure 2:
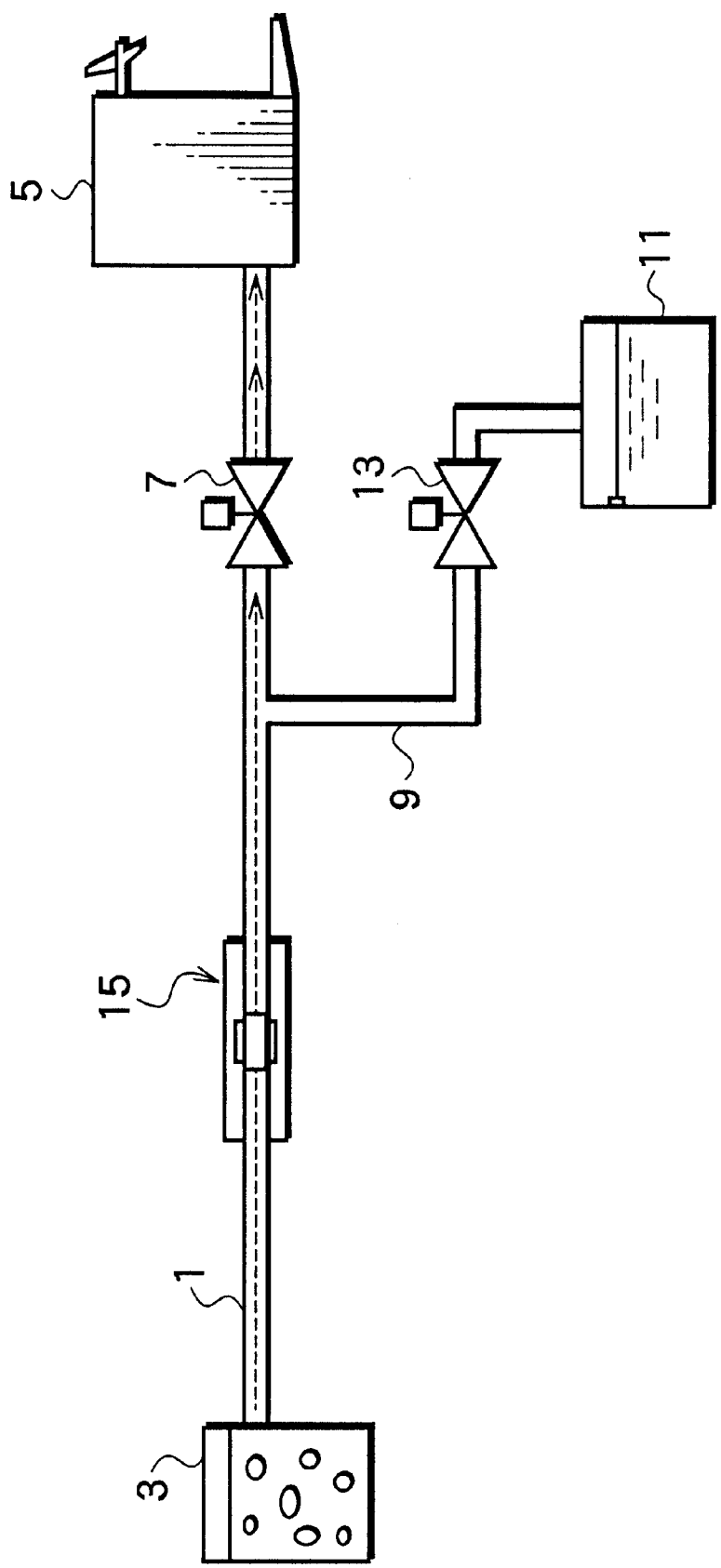
FIG. 2 is a schematic constitutional diagram of a piping fluid control system according to an embodiment of the invention.

FIG. 2 is a schematic illustration of an entirety of a piping fluid control system according to an embodiment of the invention, in which a piping 1 is adapted as illustrated to conduct a fluid substance, for example beer, to be sent through an inside path thereof.

The piping 1 is connected at one end thereof to a beer tank 3, and at a terminal of the other end to a beer take-out machine 5 as a substance take-out machine. On the way to the beer take-out machine 5 end of the piping 1 is installed a first electromagnetic open-close valve 7, which is a adjust means as a first open-close valve to be interposed between a position of the substance take-out machine and a position of a later-described electrostatic capacity sensor. The first electromagnetic open-close valve 7 allows controlling a fluid state of beer as a fluid substance flowing the path in the piping 1. That is, when the first electromagnetic open-close valve 7 is opened, beer of the piping 1 is sent to the beer take-out machine 5. When the first electromagnetic open-close valve 7 is closed, the sending of beer to the beer take-out machine 5 is stopped.

To the piping 1 is connected a drain pipe 9 as a branch pipe upstream of the first electromagnetic open-close valve 7, to be interconnected between the position of the first open-close valve and the position of the electrostatic capacity sensor to be later-described. At a terminal of the drain pipe 9 is provided a drain tank 11. On the drain pipe 9 is installed a second electromagnetic open-close valve 13, which is a adjust means as a second open-close valve to be provided for the drain pipe 9.

If the second electromagnetic open-close valve 13 is opened when the first electromagnetic open-close valve 7 is close by later-described control, beer (mainly froth) of the path in the piping 1 is discharged into the tank 11. If the first electromagnetic open-close valve 7 is opened and the second electromagnetic open-close valve 13 is closed, the discharge of the froth of beer from the piping 1 to the tank 11 stops.

Outside the piping 1 is fit a sensor unit 15 as an electrostatic capacity sensor. The sensor unit 15 is adapted to detect variations of an electrostatic capacity of the path in he piping 1. The sensor unit 15 is configured as shown in FIG. 3 to FIG. 5 for example.

Figure 3:
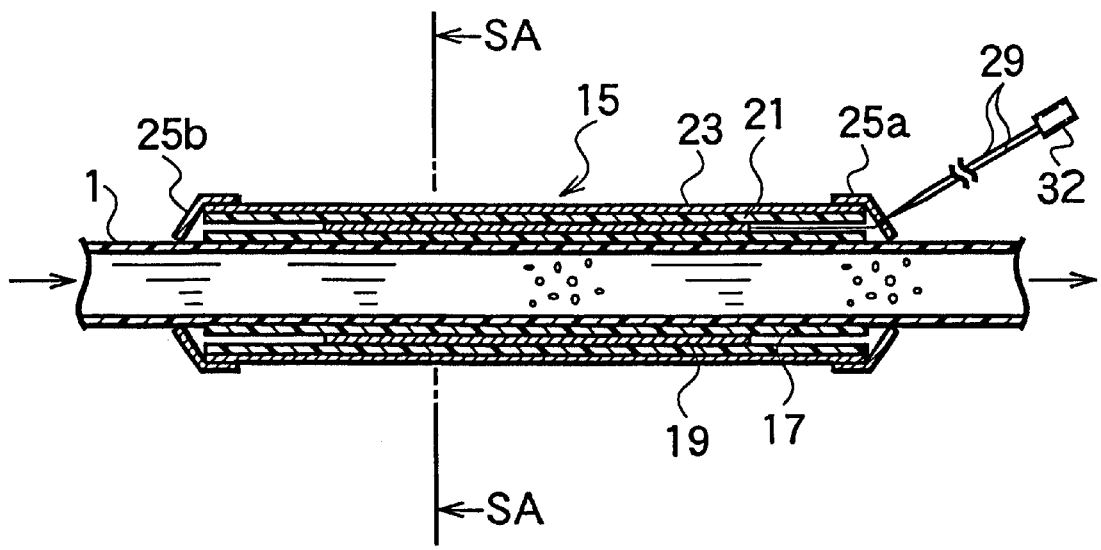
FIG. 3 is a sectional view of a sensor unit and associated parts of the piping fluid control system of FIG. 2.
Figure 4:
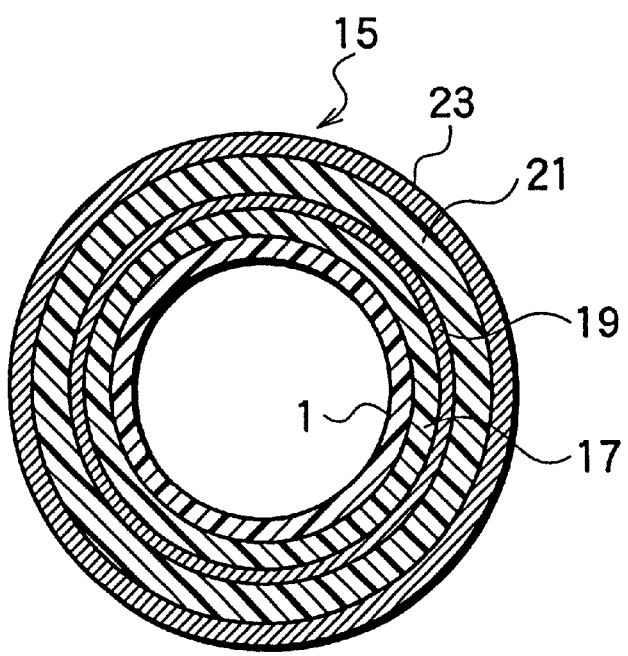
FIG. 4 is a detailed section along line SA—SA of FIG. 3.
Figure 5:
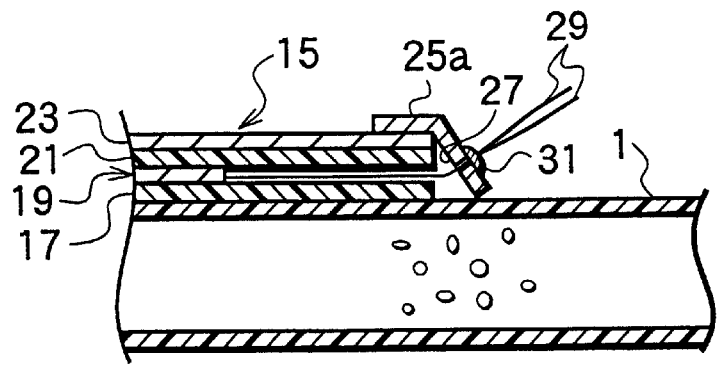
FIG. 5 is a detailed section of an essential part of the sensor unit of FIG. 3.

FIG. 3 is a sectional view of the sensor unit 15 and associated parts of the piping fluid control system, FIG. 4 is a detailed section along line SA—SA of FIG. 3, and FIG. 5 is a detailed section of an essential part of FIG. 3. As shown in FIG. 3 to FIG. 5, the sensor unit 15 is constituted with an electrode 19 wound on an outside of the piping 1 defining the path, with an inner insulator 17 in between.

In this embodiment, the insulator 17 is made as a vinyl chloride pipe. The insulator 17 is tight fit on an outside circumference of the piping 1. An adhesive or the like may be used for a fixing in place of the fitting. Like this, by use of the vinyl chloride pipe as an insulator 17, the sensor unit 15 can be assembled to the piping 1, for an integral handling therewith, as well as for a facilitated application thereto. The piping 1 is made of an insulating resin, such as vinyl chloride, at least at a portion thereof corresponding to the sensor unit 15, and may well be wholly made of an insulating resin.

The electrode 19 is made of a conductive metallic sheet to be configured as later-described. Outside the electrode 19 is provided a shield member 23, with an outer insulator 21 in between. The insulator 21 also is constituted with a pipe made of vinyl chloride. The insulator 21 tight covers an outside of the electrode 19. The insulator 21 may well be constituted as a resin mold. In some cases, the inner insulator 17 may also be constituted as a resin mold.

In this embodiment, the shield member 23 is made as an aluminum pipe. The shield member 23 is tight fit on an outside of the insulator 21. On both ends of the shield member 23 are fixed end shield members 25a and 25b. The end shield members 25a and 25b are made of aluminum in this embodiment.

One end shield member 25a is formed with a through hole 27 for drawing out lead wires 29 of the electrode 19. Between the shield member 25a and the lead wires 29 is filled with a resin mold 31. The lead wires 29 have at their ends connectors 32 for external connection.

Figure 6:
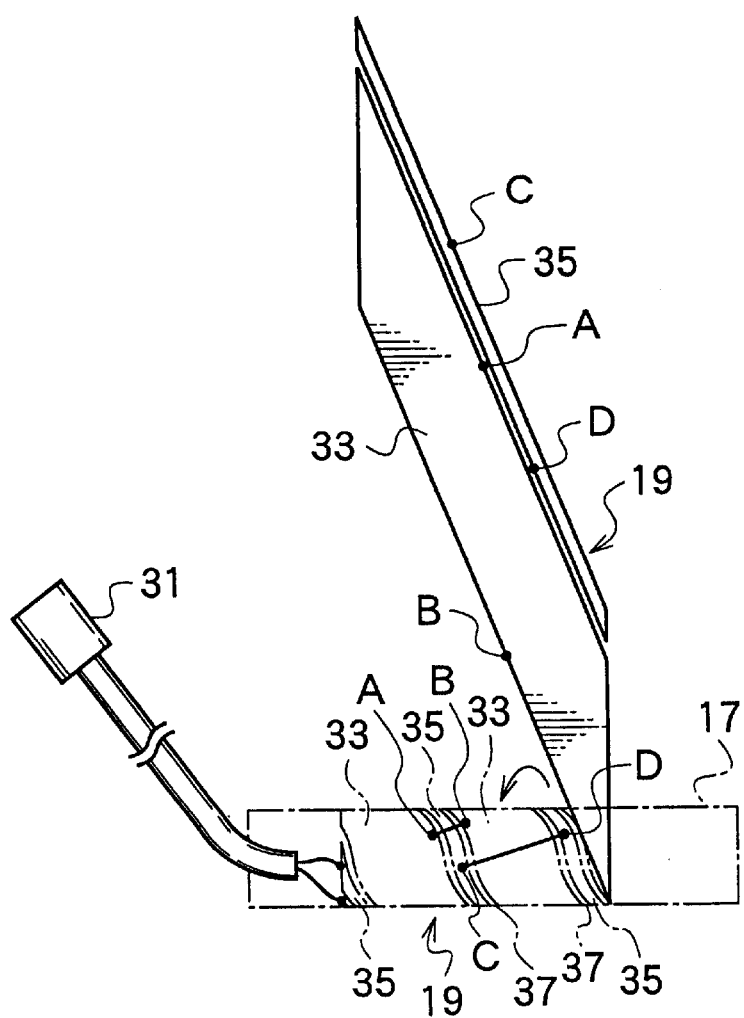
FIG. 6 is an illustration of an electrode being wound.

FIG. 6 shows how the electrode 19 is constituted. In FIG. 6, the electrode 19 is shown by one-dot-chain lines, as it is wound on the insulator 17 of vinyl chloride pipe, or by solid lines, as it is developed. As in FIG. 6, the electrode 19 is constituted with a measuring electrode 33 and a grounding electrode 35. Both the electrodes 33 and 35 are made as a substantially parallelogram belt-shaped copper film. A sum of lengths of the short sides (left or right vertical sides in solid line in FIG. 6) of the electrodes 33 and 35 and a later-described gap 37 between the electrodes 33 and 35 is substantially equal to the length of an outside circumference of the insulator 17.

The grounding electrode 35 is narrower than the measuring electrode 33. The measuring electrode 33 as well as the grounding electrode 35 is wound on the outside circumference of the insulator 17 in a spiral form along a flow direction as shown by one-dot-chain lines, and fixed by use such as of an adhesive. The number of turns in this embodiment is about three rounds along the outside circumference of the insulator 17. However, so long as a variation of electrostatic capacity is detectable over an entire circumference of the piping 1 by the electrodes 33 and 35, the number of turns may be arbitrarily selected. The electrodes 33 and 35, as they are wound on the insulator 17, have a gap 37 provided therebetween.

The electrodes 33 and 35 are alternately disposed, when wound on the insulator 17. In this condition, neighboring wound parts of the electrode 33 are mutually short-circuited between short-circuit points A and B. In the case of electrode 35, wound parts are short-circuited between short-circuit points C and D. In such wound condition of the electrode 19 in FIG. 6, the short-circuit points A, B, C, and D are positioned on the same side for convenient concurrent illustration, while actually the short-circuit points A, B, C, and D are located on positions shown in the developed state.

Figure 7:
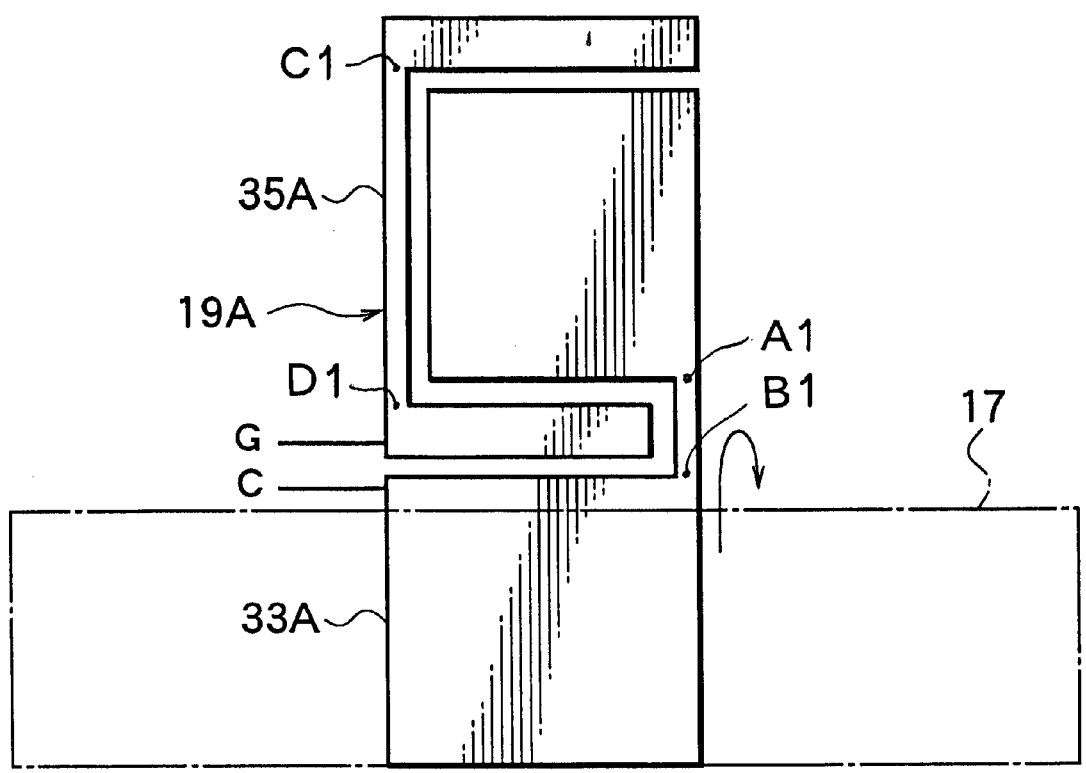
FIG. 7 is an exploded view of an electrode corresponding to the electrode of FIG. 6.

Such arrangement provides an electrode constitution analogous in disposition to an electrode 19A of FIG. 7, for example. In the electrode 19 of FIG. 6, the short-circuit points A, B, C, and D correspond in position to points A1, B1, C1, and D1 in the electrode 19A, whereas by provision of the substantially parallelogram belt-shaped electrodes 33 and 35 short-circuited at the short-circuit points A, B, C, and D, it is allowed for the electrode 19 to be spirally wound on the outside of the insulator 17.

It also is possible as a matter of course to use arrangement of the electrode 19A of FIG. 7 in place of the electrode 19. In FIG. 7, the electrode 19A is constituted with a measuring electrode 33A and a grounding electrode 35A both wound around a whole circumference on an outside of the insulator 17. The electrodes 19 and 19A of FIG. 6 and FIG. 7 are different from each other in that in the case of electrode 19 spirally wound on an outside of the insulator 17 as shown in FIG. 6, variations of electrostatic capacity due to a flow of a fluid substance such as beer in the path of the piping 1 can be detected more correctly and easily.

Figure 8:
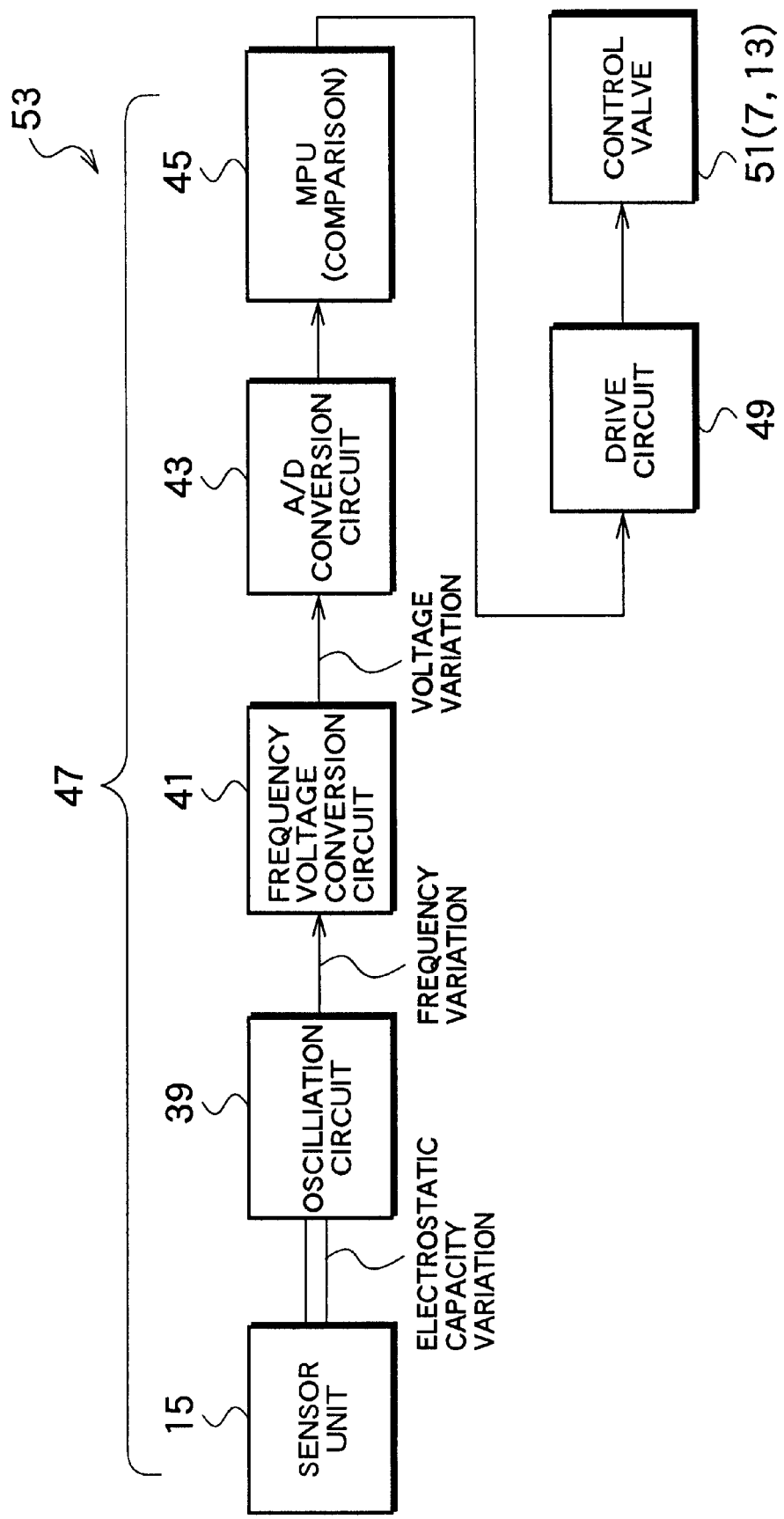
FIG. 8 is a block diagram of the piping fluid control system.

FIG. 8 is a schematic block diagram of the piping fluid control system 53 including a piping fluid decision device 47. The piping fluid decision device 47 is constituted with the sensor unit 15, an oscillation circuit 39, a frequency voltage conversion circuit 41, an A/D conversion circuit 43, and an MPU 45. The piping fluid control system 53 is constituted with the piping fluid decision device 47, a drive circuit 49, and a control valve 51. The control valve 51 is constituted with the first and second electromagnetic open-close valve 7 and 13 of FIG. 2. The MPU 45 constitutes a control means for controlling the control valve 51 as a adjust means.

In the MPU 45 is stored in advance a reference variation of electrostatic capacity of the path in the piping 1 when the fluid substance flows in the path. The reference variation of electrostatic capacity is used for a decision on a fluid condition, for example to be normal or abnormal, of the fluid substance flowing the path in the piping 1. In this embodiment, a variation of electrostatic capacity between when beer flowing the path in the piping 1 has a liquid state (to be normal) and when it has a froth state (to be abnormal) is stored as the reference variation of electrostatic capacity. Therefore, the MPU 45 in this embodiment constitutes a reference value storage means. A value of the reference variation of electrostatic capacity is arbitrarily adjustable in dependence such as on an amount of froth desired to be flown to the beer take-out machine 5 end. The MPU 45 is adapted for comparing a detected variation of electrostatic capacity with the stored variation of electrostatic capacity to decide the fluid state of beer flowing in the path in the piping 1. Therefore, the MPU 45 in this embodiment constitutes a fluid decision means.

If the sensor unit 15 detects a variation of electrostatic capacity, this is input as a frequency variation corresponding to the variation of electrostatic capacity from the oscillation circuit 39 to the frequency voltage conversion circuit 41. The frequency voltage conversion circuit 41 converts the input frequency variation into a voltage variation, and inputs this to the A/D conversion circuit 43. The A/D conversion circuit 43 replaces the input voltage variation with a digital signal of a binary number value, and inputs this to the MPU 45. At the MPU 45, an input variation of electrostatic capacity by detection is compared with a set reference variation of electrostatic capacity.

The MPU 45 depends on a result of the comparison to decide whether the fluid state of beer flowing in the path is a liquid state or a froth state, and outputs this decision to the drive circuit 49. The drive circuit 49 controls the control valve 51 by the output from the MPU 45.

As shown in FIG. 2, beer from the beer tank 3 flows inside the piping 1, and when this is sent to the beer take-out machine 5, a variation of electrostatic capacity of the path in the piping 1 is detected at the sensor unit 15. By this detection, while liquid beer is flowing in the piping. 1, because the variation of electrostatic capacity is little or less than the set value, a corresponding signal is sent from the MPU 45 via the drive circuit 49 to the first and second electromagnetic open-close valve 7 and 13, so that the first electromagnetic open-close valve 7 is opened and the second electromagnetic open-close valve 13 is closed, allowing for beer of a liquid state to be sent to the beer take-out machine 5.

If the beer flowing through the path in the piping 1 enters a froth state, a variation of electrostatic capacity is detected at the sensor unit 15. A result of this detection is compared in the MPU 45, with a result, whereby a signal is output via the drive circuit 49 to the control valve 51, so that the first electromagnetic open-close valve 7 is closed and the second electromagnetic open-close valve 13 is opened.

As a result, the froth state beer flowing through the path in the piping 1 is wasted via the drain pipe 9 to the drain tank 11. By such control, it is ensured that liquid beer little of froth can be taken out from the beer take-out machine 5. Depending on a setting of a reference variation of electrostatic capacity at the MPU 45, it is possible to control the amount of froth mixed in liquid beer to be taken out from the beer take-out machine 5, or the like.

Because the fluid state of beer flowing though the path in the piping 1 can be intact-detected, electrodes are free from corrosion or such, permitting beer flowing in the piping 1 to be kept at a high sanitary condition. Because the variation of electrostatic capacity provides a great voltage variation, it is unnecessary to integrate a detection result, allowing for a small calculation amount to perform a rapid and correct control, permitting the system also to be compact.

Because the fluid state is detected as a variation of electrostatic capacity, the magnetic field hardly influences, allowing for example for the sensor unit 15 to be disposed in a vicinity of the first electromagnetic open-close valve 7, permitting an increased design flexibility.

Figure 9:
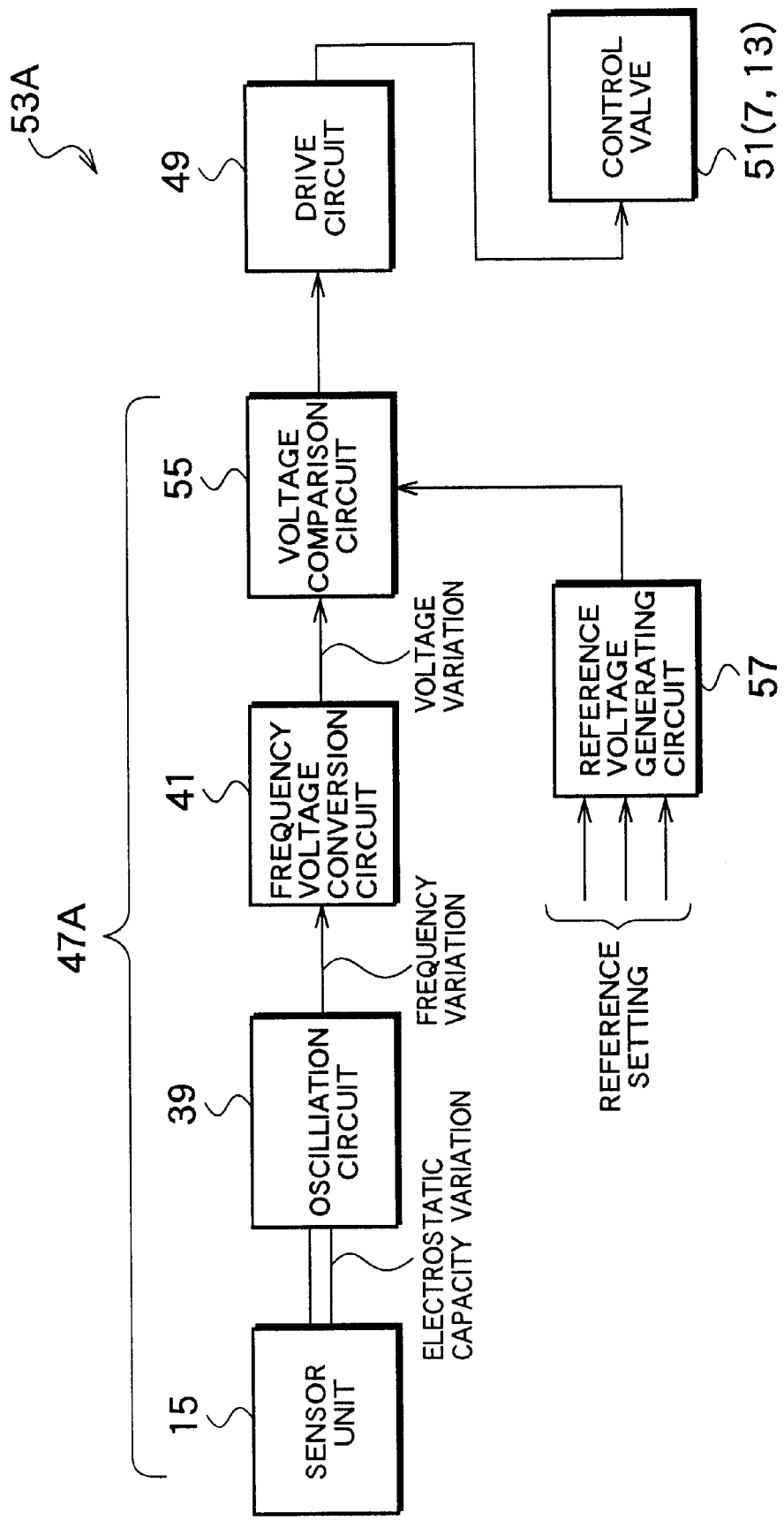
FIG. 9 is a block diagram of a piping fluid control system according to another embodiment of the invention.

FIG. 9 shows a piping fluid control system 53A according to a modification of the above embodiment, as another embodiment of the invention. In FIG. 9, component parts corresponding to FIG. 8 are designated by like reference characters. In the piping fluid control system 53A of FIG. 9, there are provided a voltage comparison circuit 55 and a reference voltage generating circuit 57 in place of the A/D conversion circuit 43 and the MPU 45 of FIG. 8.

A piping fluid decision device 47A is constituted with a sensor unit 15, an oscillation circuit 39, a frequency voltage conversion circuit 41, the voltage comparison circuit 55, and the reference voltage generating circuit 57.

The reference voltage generating circuit 57 is for generating a reference voltage to be compared at the voltage comparison circuit 55, and generates a reference voltage corresponding to a reference variation of electrostatic capacity to be set. Therefore, the reference voltage generating circuit 57 in this embodiment constitutes a reference value storage means.

A reference voltage generated at the reference voltage generating circuit 57 is sent to the voltage comparison circuit 55, where it is compared with a voltage variation corresponding to a detected variation of electrostatic capacity, to output a signal, depending on a comparison result, via a drive circuit 49 to a control valve 51. Therefore, the voltage comparison circuit 55 in this embodiment constitutes a fluid decision means and a control means.

Also, in the embodiment of FIG. 9, while the variation of electrostatic capacity is little or small, a first electromagnetic open-close valve 7 is opened and a second electromagnetic open-close valve 13 is closed. If the variation of electrostatic capacity exceeds a set value, the first electromagnetic open-close valve 7 is closed and the second electromagnetic open-close valve 13 is opened. Therefore, in the circuit arrangement of FIG. 9 also, beer can be securely sent to a beer take-out machine 5 when the state of beer flowing in a piping 1 is a liquid state, or securely wasted to a drain tank 11 when it is a froth state.

In the foregoing embodiments, although a drain pipe 9 as a branch pipe is connected between the sensor unit 15 and the first electromagnetic open-close valve 7, the first electromagnetic open-close valve 7 may be a 3-way valve and a drain pipe 9 may be connected to the 3-way valve, so that by a port-switching of the 3-way valve by way of an electrical switching control by a control means, a flow from the piping 1 to the beer take-out machine 5 end and a flow from the piping 1 to the drain tank 11 end can be changed over.

In the foregoing embodiments, although the sensor unit 15 is fitted on the linear piping 1, the fitting may be performed to a piping 1 with a corner part or to the corner part with ease by use such as of soft insulators 17 and 21 and a soft shield member 23. In such a case, the spiral winding of the electrode 19 allows an ensured arrangement of the electrode 19 along the corner part of the piping 1.

The electrodes 19 and 19A may be directly wound on a piping 1 made of a vinyl chloride pipe or the like, thereby eliminating the inner insulator 17.

In the foregoing embodiments, although beer is applied as a fluid substance, any fluid substance else may be applied. For example, a liquid body such as water or oil, a gaseous body such as air or carbon dioxide, or a solid body such as a metallic flow, a soil flow, a stone flow, or beans may be judged for the fluid state to perform a predetermined separation control or the like.

For example, in case of a cleaning of a food tank to be performed in order of a water cleaning, a hot water cleaning, a germicidal agent cleaning, or such, there may be stored as reference values in advance those variations of electrostatic capacity which a piping for sending them has when water, hot water, a germicidal agent, or such flows therein, and in a service a variation of electrostatic capacity in the piping may be detected by a sensor unit and compared with a reference value, so that it is ensured to judge which of the water, hot water, and the germicidal agent is used for a current cleaning of the tank. That is, the fluid state of fluid substance contains a change of kind of the fluid substance.

A plurality of branch pipes may be connected to a single piping, and the kind of a fluid substance may be detected by a variation of electrostatic capacity, so that it is ensured to deliver a different kind of fluid substance from the piping to a respective branch pipe.

The decision by comparison of electrostatic capacity is considered to cover, not simply a comparison decision of its variation value, but also the electrostatic capacity itself to be within an equivalent scope.

What is claimed is:

1. A piping fluid decision device comprising:
   an electrostatic capacity sensor disposed outside of a piping adapted for a fluid substance to flow through a path therein, for detecting a variation of electrostatic capacity of the path in the piping;
   reference value storage means for storing in advance a reference variation of electrostatic capacity of the path to provide for a decision on a fluid state of the fluid substance flowing through the path in the piping; and fluid decision means for comparing the detected variation of electrostatic capacity and the stored variation of electrostatic capacity to make the decision on the fluid state of the fluid substance flowing through the path;

wherein the electrostatic capacity sensor comprises a measuring electrode and a grounding electrode made of a conductive metallic film and wound around an outside of the piping forming the path, with an insulator in between, and a shield member covering the measuring electrode and the grounding electrode, with an insulator in between; and the grounding electrode is narrower than the measuring electrode, and the measuring electrode and the grounding electrode are alternately disposed and are wound to be spiral along a flow direction.

2. A piping fluid control system decision device comprising:

a piping fluid decision device according to claim 1;

adjust means adapted to adjust the fluid state of the fluid substance flowing through the path; and control means for controlling the adjust means depending on a result of the decision of the fluid decision means.

3. A piping fluid control system according to claim 2, wherein the piping is provided at a terminal thereof with a substance take-out machine of the fluid substance, the adjust means comprises a first open-close valve installed on the piping between an electrostatic capacity sensor position and a substance take-out machine position, and a second open-close valve installed on a branch pipe connected to the piping between a position of the first open-close valve and the electrostatic capacity sensor position, and the control means is adapted, when the variation of electrostatic capacity is within a set value, to open the first open-close valve and close the second open-close valve and, when the variation of electrostatic capacity exceeds the set value, to close the first open-close valve and open the second open-close valve.

* * * * *